(12) United States Patent
Plihal et al.

(10) Patent No.: US 9,714,905 B1
(45) Date of Patent: Jul. 25, 2017

(54) WAFER INSPECTION RECIPE SETUP

(71) Applicant: KLA-Tencor Corporation, Milpitas, CA (US)

(72) Inventors: Martin Plihal, Pleasanton, CA (US);
Deepak Gupta, San Jose, CA (US);
Vidyasagar Anantha, Hyderabad (IN);
Premkumar Vijayaraman, Chennai (IN); Lakshman Deenadayalan, Chennai (IN)

(73) Assignee: KLA-Tencor Corp., Milpitas, CA (US)

( * ) Notice: Subject to any disclaimer, the term of this patent is extended or adjusted under 35 U.S.C. 154(b) by 492 days.

(21) Appl. No.: 14/311,270

(22) Filed: Jun. 21, 2014

Related U.S. Application Data

(60) Provisional application No. 61/838,333, filed on Jun. 23, 2013.

(51) Int. Cl.
*G01N 21/95* (2006.01)

(52) U.S. Cl.
CPC .................. *G01N 21/9501* (2013.01)

(58) Field of Classification Search
CPC .................................. G01N 21/9501
USPC ........................................... 702/40
See application file for complete search history.

(56) References Cited

U.S. PATENT DOCUMENTS

| | | | |
|---|---|---|---|
| 6,424,881 B1 | 7/2002 | Steffan et al. | |
| 8,000,922 B2 | 8/2011 | Chen et al. | |
| 8,045,786 B2 | 10/2011 | Widmann et al. | |
| 8,049,877 B2 | 11/2011 | Wallingford et al. | |
| 8,126,255 B2 | 2/2012 | Bhaskar et al. | |
| 2007/0156379 A1* | 7/2007 | Kulkarni | H01L 21/67005 703/14 |
| 2011/0320149 A1* | 12/2011 | Lee | G01N 21/9501 702/83 |
| 2014/0241610 A1 | 8/2014 | Duffy et al. | |
| 2014/0376801 A1* | 12/2014 | Karsenti | G06T 7/001 382/145 |

(Continued)

FOREIGN PATENT DOCUMENTS

| | | |
|---|---|---|
| EP | 2 195 834 | 6/2010 |
| EP | 2 289 096 | 3/2011 |

(Continued)

*Primary Examiner* — Bryan Bui
(74) *Attorney, Agent, or Firm* — Ann Marie Mewherter

(57) ABSTRACT

Methods and systems for setting up a wafer inspection recipe are provided. Inspection results produced by complete wafer inspection recipe candidates, each of which includes one or more optical mode candidates with at least one set of defect detection parameters, are compared to determine which of the complete wafer inspection recipe candidates is the best for use as the wafer inspection recipe. The method does not involve making any decisions regarding performance of the complete wafer inspection recipe candidates until after the inspection results have been compared. In other words, the method does not involve selecting optical mode(s) that will be used in the wafer inspection recipe followed by selecting the defect detection parameters for the selected optical mode(s). In this manner, a greater number of optical mode and defect detection parameters can be considered in an efficient manner to determine the best wafer inspection recipe for any given wafer.

31 Claims, 3 Drawing Sheets

(56) References Cited

U.S. PATENT DOCUMENTS

2015/0006103 A1\* 1/2015 De Wel .................. H01L 22/12
                                                         702/123

FOREIGN PATENT DOCUMENTS

WO    2009/039486    3/2009
WO    2009/148876    12/2009

\* cited by examiner

WAFER INSPECTION RECIPE SETUP

BACKGROUND OF THE INVENTION

1. Field of the Invention

The present invention generally relates to methods and systems for setting up wafer inspection recipes.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Many different types of inspection systems have adjustable output acquisition (e.g., data, signal, and/or image acquisition) and sensitivity (or defect detection) parameters such that different parameters can be used to detect different defects or avoid sources of unwanted (nuisance) events. Although an inspection system that has adjustable output acquisition and sensitivity parameters presents significant advantages to a semiconductor device manufacturer, these inspection systems are essentially useless if the incorrect output acquisition and sensitivity parameters are used for an inspection process. In addition, since the defects, process conditions, and noise on wafers may vary dramatically (and since the characteristics of the wafers themselves may vary dramatically), the best output acquisition and sensitivity parameters for detecting the defects on a particular wafer may be difficult, if not impossible, to predict. Therefore, although using the correct output acquisition and sensitivity parameters will have a dramatic effect on the results of inspection, it is conceivable that many inspection processes are currently being performed with incorrect or non-optimized output acquisition and sensitivity parameters.

Accordingly, it would be advantageous to develop systems and methods for setting up wafer inspection recipes that do not have one or more of the disadvantages described above.

SUMMARY OF THE INVENTION

The following description of various embodiments is not to be construed in any way as limiting the subject matter of the appended claims.

One embodiment relates to a method for setting up a wafer inspection recipe. The method includes scanning a wafer with a wafer inspection tool and a number of optical mode candidates for the wafer inspection recipe thereby generating output for the wafer for each of the optical mode candidates. The method also includes, for a first of the optical mode candidates, applying different sets of defect detection parameters to the output generated with the first of the optical mode candidates thereby producing different inspection results for the first of the optical mode candidates. In addition, the method includes storing the first of the optical mode candidates with each of the different sets of defect detection parameters as one or more of a number of complete wafer inspection recipe candidates. The method further includes repeating the applying and storing steps for at least one other of the optical mode candidates. The method also includes comparing the inspection results generated with the complete wafer inspection recipe candidates to each other. No decisions regarding performance of the complete wafer inspection recipe candidates are made until after the comparing step is performed. In addition, the method includes determining which of the complete wafer inspection recipe candidates produced the inspection results that are the best. The method further includes selecting the complete wafer inspection recipe candidate that produced the best inspection results for use as the wafer inspection recipe. The applying, storing, comparing, determining, and selecting steps are performed with one or more computer systems.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for setting up a wafer inspection recipe. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to set up a wafer inspection recipe. The system includes an optical subsystem configured to scan a wafer with a number of optical mode candidates for the wafer inspection recipe thereby generating output for the wafer for each of the optical mode candidates. The system also includes one or more computer subsystems configured for performing the applying, storing, repeating, comparing, determining, and selecting steps described above. Each of the embodiments of the system described above may be further configured as described further herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
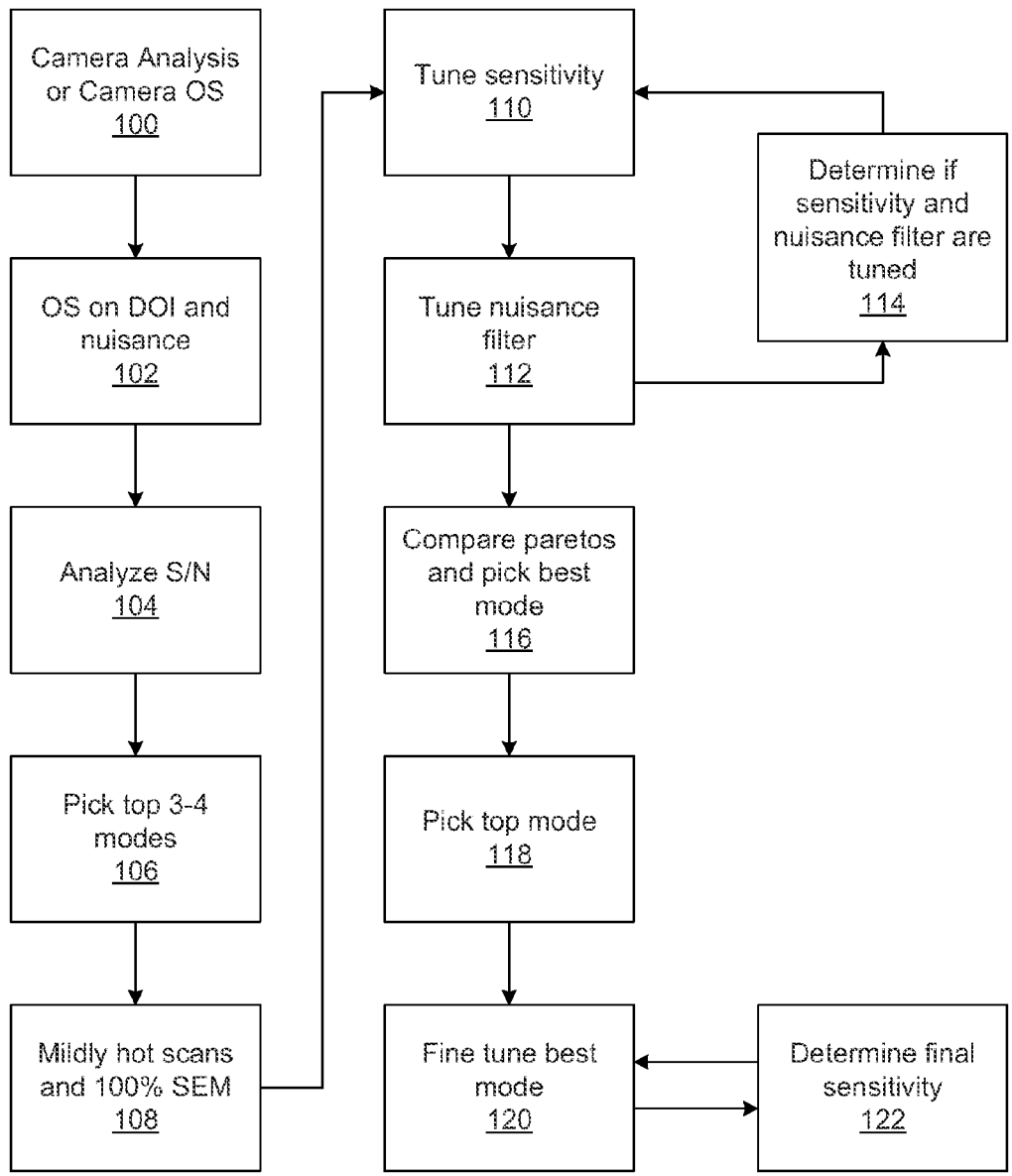
FIG. 1 is a flow chart illustrating one example of a currently used method for setting up a wafer inspection recipe.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a method for setting up a wafer inspection recipe. "Inspection" or "wafer inspection" as those terms are used herein can be generally defined as a process performed on a wafer to discover defects on the wafer. In this manner, "inspection" is different than "defect review" in that inspection involves searching for previously undetected defects on a wafer while defect review involves re-detection of previously detected defects. In other words, inspection involves detecting the unknown while review involves determining more information about the known (defects). In still other words, inspection is performed without any knowledge of the defects that may or may not be present on a wafer while defect review is performed based on information about defects previously detected on a wafer. "Inspection" is also different than "metrology" or measurement processes in that inspection involves looking at multiple locations for defects that may or may not be there while metrology involves performing one or more particular measurements at one or more particular locations. The wafer inspection is described herein in terms of optical or light-based wafer inspection although the embodiments can be used for other types of wafer inspection such as electron beam (e-beam) wafer inspection.

The embodiments described herein may be used for optimizing sensitivity of optical wafer inspection tools and improving their production performance. For example, the embodiments described herein address the issue of a growing gap between potential and achievable sensitivity of optical wafer inspection. The source of this problem is (a) the exploding number of optical and detection settings on modern high-performance optical inspection tools and (b) the increasing difficulty with which the best combination of inspection settings can be found. The embodiments described herein provide a computer-assisted recipe setup analyzer that enables tool operators (application engineers, field engineers, as well as users of all training levels) to setup highly sensitive recipes in an objective and efficient manner using intuitive criteria directly related to the ultimate inspection goals.

Optical wafer inspection systems struggle to maintain their sensitivity to ever smaller defects in the context of shrinking design rules, similarly to photolithography where the physical resolution limits imposed by the wavelength of incident light are constantly being expanded by employing creative resolution enhancement techniques (RETs). The inspection challenges are being met not only through hardware improvements such as better stage accuracy, more powerful and diverse light sources, and innovative optical solutions, but also through improvements in defect detection and nuisance removal algorithms. Another trend for the most critical layers is the increasing reliance on multi-pass inspections that combine signals from diverse optics modes to improve the discrimination between nuisance and killer defects, etc. As a result of these developments, the myriad of new setup options leaves users with the daunting task of setting up, tuning, and maintaining stable inspection recipes that are capable of detecting the most important killer defects.

The embodiments described herein provide a number of improvements and advantages including that they enable analysis of a significantly larger set of inspection configurations, simplify human involvement in the process, and provide tool operators with an objective way to evaluate the top inspection setup candidates.

In terms of the current setup methodology, although it is impossible to summarize completely the existing diverse processes of inspection setup in terms of a fixed set of steps, a typical recipe setup flow is shown in FIG. 1. In most instances, setting up a wafer inspection recipe involved finding defects of interest (DOI) on a wafer. This may be performed as described further herein. The example method shown in FIG. 1 includes a mode selection phase, which includes step 100 in which camera analysis or camera optical setup (OS) is performed. Mode selection also includes step 102 in which OS is performed on DOI and nuisance defects on a wafer. OS may be performed for as many optical modes as are available on the wafer inspection system (e.g., about 100 modes). In other words, the OS may be performed for the entire optics mode set for the wafer inspection system. Mode selection further includes step 104 in which the signal-to-noise ratios (S/N) of the DOI and nuisance defects detected by the different optical modes are analyzed. In step 106 of the mode selection phase, the top 3 or 4 optical modes are selected based on the analyzed S/N values. Mode selection also includes step 108 in which mildly hot scans are performed with the selected optical modes and all of the potential defects detected by each of the modes is reviewed (e.g., on a scanning electron microscope (SEM)). In other words, 100% SEM review of the potential defects is performed in this step.

The example method shown in FIG. 1 may also include a tuning phase in which the top modes identified in the mode selection phase are tuned. For example, this phase includes tuning sensitivity, as shown in step 110. Tuning the sensitivity may include using manually classified defects to tune various parameters of a defect detection algorithm such as segments and threshold offsets. In addition, this phase includes tuning a nuisance filter, as shown in step 112.

Tuning the nuisance filter may include using manually classified defects to tune a defect classifier over the larger space of defect attributes. The tuning phase may also include determining if the sensitivity and nuisance filter are tuned, as shown in step 114. If the sensitivity and nuisance filter are determined to not be tuned, steps 110 and 112 may be repeated until it is determined that the sensitivity and nuisance filter are tuned. In this manner, the method may include iteratively tuning the sensitivity and nuisance filter for the top optical modes.

The tuning phase also includes comparing paretos and picking the best mode, as shown in step 116. "Paretos" in this context are pareto charts or diagrams showing the number of defects detected per defect classification. Therefore, this step may include comparing the performance of the different mode/detection parameter combinations. For example, the number of different DOIs detected by each of the combinations may be compared to each other, and the number of nuisances in the inspection results may be compared to each other. In addition, the tuning phase includes picking the top mode, as shown in step 118. The tuning phase also includes fine tuning the best mode, as shown in step 120, and determining the final sensitivity, as shown in step 122. Fine tuning the best mode and determining the final sensitivity for the wafer inspection recipe may include iteratively fine tuning the sensitivity and nuisance filter on the top mode.

The main decision points and criteria of the method example shown in FIG. 1 are step 106 in which the top 3 or 4 modes are selected, step 114 in which it is determined if the sensitivity and nuisance filter are tuned, step 118 in which the top mode is selected, and step 122 in which the final sensitivity is determined. These decision points are significant, because they lead to elimination of configuration options before knowing the performance of the fully constructed recipe.

It is noted that there may be many variations to the steps shown in FIG. 1. For example, in some cases, customers may perform scans at different stages of recipe setup than indicated. They may also perform relatively crude sensitivity tuning using optical patches and then only go to the SEM to manually classify defects for nuisance filter tuning. None of these variations have a material impact on the concepts we are trying to convey.

In addition to the fact that the current inspection setup methodology is excruciatingly time consuming, tedious, and filled with repetitive manual tasks, it has some other shortcomings that the embodiments described herein do not. For example, one of the most significant disadvantages is the necessity to make decisions about setup options using criteria that do not always align with the inspection goals. In particular, optics mode selection is performed using S/N analysis and visual patch image evaluations. However, it is possible for modes with poor S/N ratios to show better separation of killer defects from nuisance in the much larger space of defect attributes employed in nuisance filters. In addition, during sensitivity tuning, some killer defects may be intentionally removed to keep the nuisance rate within specifications. Again, nuisance filters could do a better job with less aggressive settings, but such alternatives may not be fully explored under time pressure. Furthermore, due to the overwhelming number of choices encountered during recipe setup, all practical methods today rely heavily on experience from similar inspections to narrow down (or eliminate) configuration choices and on extensive training of experts. Furthermore, the number of viable setup options can be so large that, with the current methodologies, it is impossible to evaluate all but a substantially small fraction of them.

Results Fusion is a recently developed software tool for tuning recipes semi-automatically and it has some features in common with the embodiments described herein. For example, it performs nuisance filter tuning on a set of hot scans and presents multiple candidate solutions to a user for selection. Results Fusion also detunes tuning scans to prevent defect blowups in production recipes. However, Results Fusion is not integrated well into the recipe setup flow today. In addition, it does not provide any useful feedback except for nuisance rate and DOI count, and it does not allow any modification to the candidate solutions. For these reasons, Results Fusion is not widely adopted today. The embodiments described herein aim to correct these shortcomings by proposing a fully integrated solution.

The embodiments described herein rely on one fundamental principle that sets them apart from the current approaches. They rely on machine-assisted construction of a larger number of full inspection recipe "candidates" (also referred to as solutions) using the training wafer scans and user specifications. Users may still be fully in control of the recipe construction process, but the decisions about the quality of individual setup choices are deferred until after all the candidate solutions have been assembled. In other words, no decisions regarding performance of the complete wafer inspection recipe candidates are made until after comparing the inspection results generated with the complete wafer inspection recipe candidates to each other, which is described further herein, is performed. In this manner, the method does not include eliminating any of the complete wafer inspection recipe candidates prior to the comparing step described further herein. In addition, the method does not include eliminating any of the optical mode candidates prior to the comparing step described further herein. The criteria applied to the selection of good candidates may then be the same criteria that define any good wafer inspection recipe such as high sensitivity to killer defects with acceptable nuisance rate, recipe stability, matchability, etc.

It is important to note that the embodiments described herein do not necessarily replace manual recipe setup with an automated system although machine-assisted semi-automatic operation is possible in the proposed construction. For example, the Recipe Analyzer described further herein may operate by generating a number of solutions within the range of user-specified parameters. Ultimately, a user may select the one candidate they like. This can be done using configurable criteria that correspond directly to the inspection entitlement targets with the help of diagnostic information generated during the optimization process. It would also be possible to feed the diagnostics into the optimization process and thus guide the tuning process in a particular direction.

Examples of user parameters supplied to the Recipe Analyzer include: (a) selection of training scans with various optics mode settings, (b) specification of target or maximum nuisance rate, and (c) specification of defect attributes to be used for nuisance filtering and/or nuisance filter template from which users are not willing to deviate, etc.

There may also be a number of manual modes of operation (or ways to receive manual input) available in the Recipe Setup Analyzer. For example, in one embodiment, the method includes selecting at least some of the optical mode candidates and the different sets of defect detection parameters, used as described further herein, based on a wafer inspection recipe received as input from a user. In one such embodiment, the wafer inspection recipe received from the user was selected for use as the wafer inspection recipe in a previously performed iteration of the method. For example, users could take any of the machine-constructed solutions as a starting point and tweak some parts of the corresponding recipe to create a modified recipe to be evaluated using the same set of criteria as described herein. In addition, in one embodiment, at least some of the complete wafer inspection recipe candidates are received as input from a user. For example, users could create a recipe manually and insert it into the Recipe Analyzer for evaluation with the rest of the solutions. In another embodiment, the method includes selecting at least some of the optical mode candidates and the different sets of defect detection parameters based on a wafer inspection recipe received as input from a user with an instruction to generate two or more of the complete wafer inspection recipe candidates that are similar to the wafer inspection recipe received from the user. For example, users could select a promising candidate and instruct the embodiments to generate similar solutions (i.e., "Candidates-like-this").

It is important to note that not all of the complete wafer inspection recipe candidates are previously used wafer inspection recipes. For example, although the wafer inspection recipe is selected based on comparison of inspection results produced by complete wafer inspection recipe candidates, the recipe candidates do not include only previously used recipes. In other words, one could take a wafer, perform a number of inspections on it using existing wafer inspection recipes, determine which of the existing wafer inspection recipes produces the best results, and then select the recipe that produced the best results for use on the wafer and other similar wafers. However, this is fundamentally different than the embodiments described herein in that, although one or more of the wafer inspection recipes may be pre-existing recipes, because wafers and DOIs and nuisances formed thereon can have significantly different characteristics and because the best combination of optical and defect detection parameters is almost impossible to predict, simply using only pre-existing recipes as the candidates described herein would almost guarantee that the best candidate is not considered let alone selected for use in the wafer inspection recipe. In contrast, the embodiments described herein can consider many more optical mode candidates and defect detection parameters to identify the best possible wafer inspection recipe. For example, as described further herein, for any given optical mode candidate, any variation of defect detection parameters can be combined with the optical mode candidate to generate a number of different wafer inspection recipe candidates. Simply using pre-existing recipes would not allow such a large number of possibilities to be considered.

The embodiments described herein may include finding DOI that will be used for one or more steps of the method. For example, a DOI finding phase of the embodiments may include picking the initial optical modes that will be used to find the DOI. For instance, less than 10 or so of all the available optical modes on a wafer inspection system may be selected for DOI finding. The DOI finding may then include performing hot scans on a wafer (a setup wafer) using the selected initial optical modes. The potential defects that are detected by the hot scans may include a significant number of nuisances (e.g., at a 99% nuisance rate). The DOI finding phase may also include sampling the potential defects detected in the hot scans and reviewing the defects (e.g., on a SEM). The DOI finding phase may then include determining if the DOI have been found in the hot scans. If the DOI have been found, then the method may continue to the next phase described herein. If the DOI have not been found, then the method may include repeating the steps for DOI finding until the DOI have been sufficiently detected.

Figure 2:
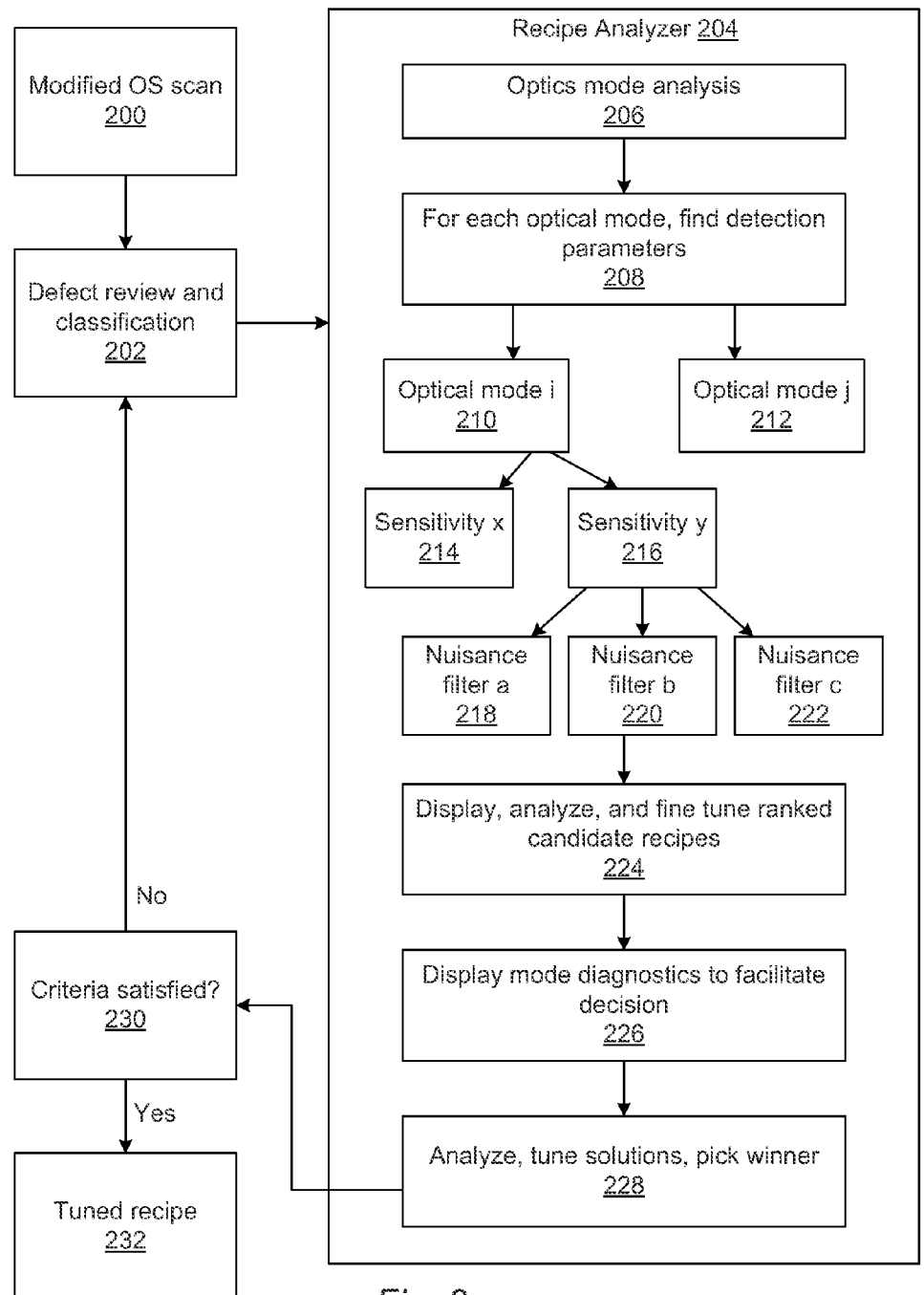
FIG. 2 is a flow chart illustrating one embodiment of a method for setting up a wafer inspection recipe.

The next phase of the embodiments may include the mode selection and tuning of modes. FIG. 2 illustrates one embodiment of a method for setting up a wafer inspection recipe. The method includes scanning a wafer with a wafer inspection tool and a number of optical mode candidates for the wafer inspection recipe thereby generating output for the wafer for each of the optical mode candidates. For example, as shown in FIG. 2, the method may include modified OS scan, as shown in step 200. In some embodiments, the optical mode candidates include all possible optical modes for use in the wafer inspection recipe. In this manner, the modified OS scan may be performed using the entire optics mode set, which for most modern wafer inspection systems is on the order of about 100 modes. However, in another embodiment, at least some of the optical mode candidates are determined based on input from a user. For example, the optics modes that are used for this step may include optics and other hardware selections made by the method (e.g., based on input from the user) or by a user. The optical mode candidates used for this step may be further determined as described herein. The modified OS scan may cover all classified defects on the wafer and a few swaths on the wafer, possibly with the detuning described further above. There is, therefore, wafer inspection system tool time required to generate the training data for the OS scans. However, it is necessary to scan only swaths with the classified defects.

As shown in step 202, the method may include defect review and classification. This step may include SEM defect review and classification of additional unique defects. Initially, if there are less than 2000 defects detected with the output generated by the modified OS scans, then all of the defects may be reviewed and classified. Otherwise, the defect review and classification may be performed to try to get a statistically meaningful sample of DOIs (e.g., 20 to 40 DOIs reviewed and classified).

The method may then proceed to the Recipe Analyzer phase 204. The input to this phase may be a single scan or multiple scans with different optics settings (modes) of the training wafer with classified defects. In this phase, optics mode analysis may be performed in step 206. The optics mode analysis may involve analyzing any of the results of the optics scans such as S/N, etc. The results of this analysis step may be kept for diagnostics to be available at the end (e.g., as additional criteria used for selecting a wafer inspection recipe candidate for use as the wafer inspection recipe).

The method includes, for a first of the optical mode candidates, applying different sets of defect detection parameters to the output generated with the first of the optical mode candidates thereby producing different inspection results for the first of the optical mode candidates. For example, as shown in step 208, the method may include, for each optical mode, finding detection parameters. The detection parameters may include any parameters of any defect detection algorithms and/or classification algorithms, which are used with the output generated by scanning the wafer, to generate inspection results for the wafer. In the case of defect detection algorithms, the detection parameters may include parameters related to defect detection sensitivity such as threshold(s) and segment break(s). In the case of classification algorithms, the detection parameters may include parameters of nuisance filter(s) and parameters of decision tree classifier(s). The method also includes repeating the applying step for at least one other of the optical mode candidates. In this manner, different sets of defect detection parameters can be applied to the output generated by each of the optical modes. As such, different inspection results can be generated for different combinations of optical mode candidates and detection parameters.

In this step, for each scan that was performed, the method may include finding sensitivity settings for various nuisance rates. Therefore, as shown in FIG. 2, the results of this step may include taking results of multiple optical modes 210 and 212 and finding different sensitivity settings for each optical mode. In addition, in one embodiment, at least some of the different sets of defect detection parameters are determined based on input from a user. For example, as described above, examples of user parameters supplied to the Recipe Analyzer include specification of target or maximum nuisance rate and specification of defect attributes to be used for nuisance filtering and/or nuisance filter template from which users are not willing to deviate, etc. In another embodiment, applying the different sets of defect detection parameters to the output includes comparing the inspection results produced with a first of the different sets to user-specified targets for the inspection results, altering the first of the different sets based on results of comparing the inspection results produced with the first of the different sets thereby generating a second of the different sets of defect detection parameters, and performing the steps of the applying step with the second of the different sets. In this manner, the method may include generating a number of sensitivity settings within user-specified parameters for each optics mode. In addition, the method may include iteratively trying different defect detection parameters until at least some defect detection parameters have been found for each mode that produce inspection results within user-specified criteria. For example, as shown in FIG. 2, the method may include finding sensitivity settings 214 and 216 for optical mode i. Sensitivity settings (not shown) may also be found for optical mode j and any other optical modes that were used for scans in step 200. Although two sensitivity settings, sensitivity x and sensitivity y, are shown in FIG. 2 as being determined for optical mode i, any number of different sensitivity settings may be determined for each optical mode. In addition, for each sensitivity setting, a number of different nuisance filters 218, 220, and 222 may be identified. For example, for sensitivity y, nuisance filters a, b, and c have been identified. Although not shown in FIG. 2, nuisance filters may also be identified for sensitivity x and any other sensitivity settings determined for optical mode i, optical mode j, and any other optical modes being analyzed. In this manner, multiple nuisance filters may be generated for each mode and sensitivity combination. The nuisance filters may be generated such that the results of different mode and sensitivity combinations are within user specifications. In addition, different nuisance filters may also be generated for pairs or combinations of modes that may be used together in a wafer inspection recipe.

The method includes storing the first of the optical mode candidates with each of the different sets of defect detection parameters as one or more of a number of complete wafer inspection recipe candidates. This storing step is also repeated for at least one other of the optical candidates. For example, the method then includes generating the candidate recipes, where each candidate recipe is one combination of optics mode(s), sensitivity setting(s), and nuisance filter(s). In one such example, in the embodiment shown in FIG. 2, one candidate recipe would be optical mode i, sensitivity y, and nuisance filter a. Another candidate recipe would be optical mode i, sensitivity y, and nuisance filter b. An additional candidate recipe would be optical mode i, sensitivity y, and nuisance filter c. Similar candidate recipes can be generated for the combination of optical mode i and sensitivity x. In addition, candidate recipes can be generated for optical mode j and any combinations of sensitivity settings and nuisance filters determined for that optical mode. In this manner, the output of this step may be a mapping of the input and user parameters into a larger set of candidate recipes that are fully constructed (i.e., ready and able to be used as actual wafer inspection recipes). The complete wafer inspection recipe candidates may be stored in any of the storage media described further herein and in any file format, data structure, etc.

The method also includes comparing the inspection results generated with the complete wafer inspection recipe candidates to each other. In addition, the method includes determining which of the complete wafer inspection recipe candidates produced the inspection results that are the best. The method further includes selecting the complete wafer inspection recipe candidate that produced the best inspection results for use as the wafer inspection recipe. For example, as shown in step 224 of FIG. 2, the method may include displaying, analyzing, and fine tuning the ranked candidate recipes. In addition, as shown in step 226, the method may include displaying mode diagnostics to facilitate decision making about which is the best candidate to use as the wafer inspection recipe. For example, any of the information generated for the wafer inspection recipe candidates may be displayed to a user in a user interface. In some embodiments, the method also includes comparing the inspection results generated with the complete wafer inspection recipe candidates to requirements for the inspection results received from a user and eliminating any of the complete wafer inspection recipe candidates that did not produce inspection results that meet the requirements from the determining and selecting steps described above. In this manner, if there are some candidates that are generated that are not able to meet user requirements for the recipes, the method may eliminate those candidates from further consideration. As such, the user may be only able to select from a subset of all of the candidates that were generated. As further shown in step 228, the method may include analyzing and/or tuning the solutions and picking the "winner."

In one embodiment, the inspection results include multiple types of information for the wafer generated by each of the complete wafer inspection recipe candidates and for performance of the complete wafer inspection recipe candidates. In another embodiment, the inspection results include information for different types of defects detected on the wafer by each of the complete wafer inspection recipe candidates. For example, the embodiments described herein may compare inspection results directly related to the ultimate inspection goals that define any good wafer inspection recipe such as achievable sensitivity to killer defects with acceptable nuisance rate, recipe stability, matchability, etc. Therefore, unlike currently used wafer inspection recipe setup methods that rely on comparing intermediate results generated by inspection such as S/N for individual defects, the methods described herein may compare and rely on the type of wafer and defect information that would be included in the inspection results reported to a user, e.g., different types of DOI detected, numbers of each of the types of DOI detected, nuisance detection rate, etc.

The applying, storing, comparing, determining, and selecting steps described herein are performed with one or more computer systems, which may be configured as described further herein. In some instances, some of these steps may be performed by a user via the user interface and one or more input devices. For example, the embodiments described herein may be configured to allow user interaction for one or more of the following functions: diagnostic output, sorting, filtering, and recipe selection (e.g., using criteria on generated metrics), and manual modification of generated solutions. The embodiments described herein may be implemented with different mixes of semi-automated, computer-assisted, and manual operations. Various levels of integration of the Recipe Analyzer with inspector tools can also be considered from fully integrated to fully offline construction.

As shown in step 230, the method may include determining if the criteria is satisfied. Determining if the criteria is satisfied may include comparing the results of the "winning" candidate to any user-specified criteria for the results. If the criteria has not been satisfied, the method may go back to step 202 in which defect review and classification may be performed again, and then the recipe analyzer phase may be performed with other defects and/or other detection parameters. If the criteria has been satisfied, then the method may output the tuned recipe, as shown in step 232.

The embodiments described herein have a number of advantages over other methods and systems for setting up a wafer inspection recipe. For example, the embodiments described herein have the ability to process a much larger set of optics modes and other recipe settings. In this manner, the embodiments are capable of performing wafer inspection recipe setup in a completely different way compared to currently used methods in which one or more optics modes are selected and then the defect detection parameters are selected for the selected optic(s) modes. For example, the method does not include eliminating any of the optics modes until after complete inspection recipe candidates have been created for each optics mode. Therefore, in the candidate generation stage, different sets of defect detection parameters may be selected for each of the optics modes used for scanning. However, the methods and the selecting steps described herein do not include selecting optical parameters for use in the wafer inspection recipe followed by selecting defect detection parameters for use in the wafer inspection recipe. In other words, the methods and the selecting step do not include narrowing down the total number of optics modes being considered, followed by selection of defect detection parameters for only the remaining optics modes. As such, the performance of the optics modes in combination with different sets of defect detection parameters can be determined and compared before any of the optics modes are eliminated from consideration.

The embodiments described herein are also capable of the evaluation of each of the setup options using inspection statistics such as DOI capture, nuisance rate, and stability and separability. For example, today an optics mode may be rejected because DOIs show substantially low S/N or no signal at all in that mode although it may be possible for nuisance filters to separate DOIs from nuisance in the rejected mode better than in other modes. This property of the optics mode would be uncovered in the embodiments described herein before the mode is discarded. For instance, in one embodiment, the inspection results that are compared do not include S/N generated for defects on the wafer by more than one of the complete wafer inspection recipe candidates. Instead, as described further herein, the inspection results that are compared to select one of the candidates for use as the wafer inspection recipe include inspection results such as those that would be reported by the wafer inspection process or tool (e.g., the number of DOI captured, the number of nuisances detected, etc.).

The embodiments described herein also provide the capability for combining machine-generated recipe candidates with manually tuned recipes and comparing them using the same inspection criteria. For example, one of the machine-generated solutions may be used as a starting point for further tuning, creating a new recipe candidate, and evaluating it against all the other candidates. In addition, the embodiments described herein provide the ability to process relatively large numbers of pair combinations (i.e., combinations of optical modes) for the selected optics modes to generate two-pass inspection recipes. For example, there are 5000 pair combinations for 100 modes. Today, it is not possible to consider this many combinations. However, the embodiments described herein will make it possible to rank and search through inspection candidates for all of them.

The embodiments of the method described above may be performed by any of the system embodiments described herein. In addition, the embodiments of the methods described above may include performing any step(s) and/or function(s) of any other embodiment(s) described herein.

The method may also include storing results of any of the step(s) of the method in a computer-readable storage medium. The results may include any of the results described herein and may be stored in any manner known in the art. The storage medium may include any suitable storage medium known in the art. After the results have been stored, the results can be accessed in the storage medium and used as described herein, formatted for display to a user, used by another software module, method, or system, etc.

Figure 3:
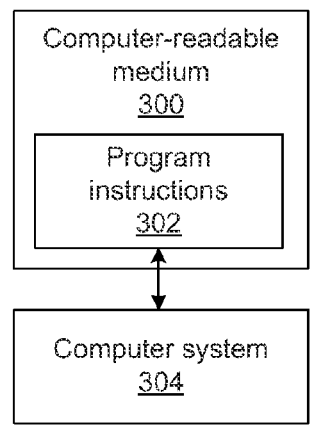
FIG. 3 is a block diagram illustrating one embodiment of a non-transitory computer-readable medium storing program instructions for causing a computer system to perform a computer-implemented method described herein.

Another embodiment relates to a non-transitory computer-readable medium storing program instructions executable on a computer system for performing a method (i.e., a computer-implemented method) for setting up a wafer inspection recipe. One such embodiment is shown in FIG. 3. For example, as shown in FIG. 3, computer-readable medium 300 stores program instructions 302 executable on computer system 304 for performing the method described above. The computer-implemented method for which the program instructions are executable may include any other step(s) of any other method(s) described herein.

Program instructions 302 implementing methods such as those described herein may be stored on computer-readable medium 300. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 304 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 4:
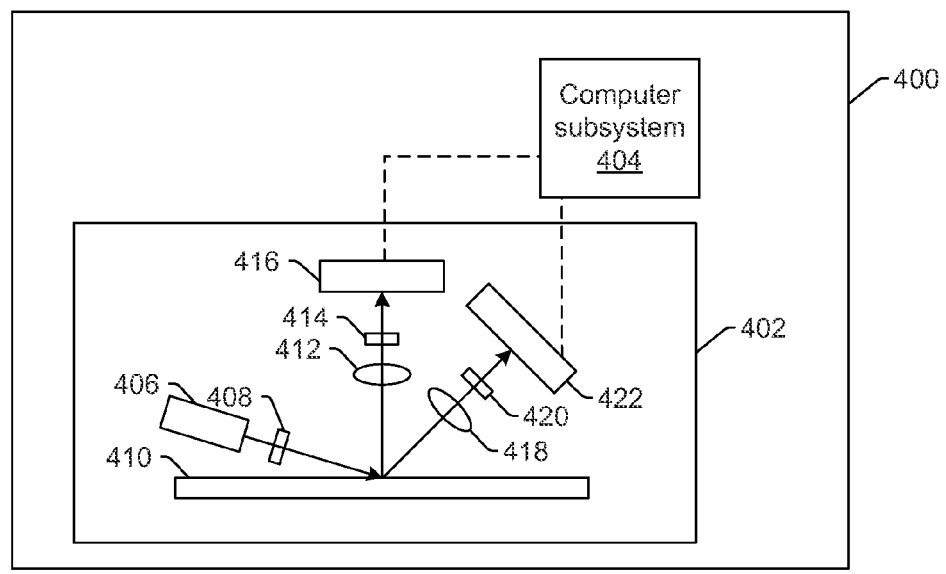
FIG. 4 is a schematic diagram illustrating a side view of an embodiment of a system configured to set up a wafer inspection recipe.

An additional embodiment relates to a system configured to set up a wafer inspection recipe. One embodiment of such a system is shown in FIG. 4. As shown in FIG. 4, system 400 includes optical subsystem 402 and computer subsystem 404. The optical subsystem is configured to scan a wafer with a number of optical mode candidates for the wafer inspection recipe thereby generating output for the wafer for each of the optical mode candidates. For example, as shown in FIG. 4, the optical subsystem includes light source 406 such as a laser. Light source 406 is configured to direct light to polarizing component 408. In addition, the optical subsystem may include more than one polarizing component (not shown), each of which may be positioned independently in the path of the light from the light source. Each of the polarizing components may be configured to alter the polarization of the light from the light source in a different manner. The optical subsystem may be configured to move the polarizing components into and out of the path of the light from the light source in any suitable manner depending on which polarization setting is selected for illumination of the wafer during a scan. The polarization setting used for the illumination of the wafer during a scan may include p-polarized (P), s-polarized (S), or circularly polarized (C).

Light exiting polarizing component 408 is directed to wafer 410 at an oblique angle of incidence, which may include any suitable oblique angle of incidence. The optical subsystem may also include one or more optical components (not shown) that are configured to direct light from light source 406 to polarizing component 408 or from polarizing component 408 to wafer 410. The optical components may include any suitable optical components known in the art such as, but not limited to, a reflective optical component. In addition, the light source, the polarizing component, and/or the one or more optical components may be configured to direct the light to the wafer at one or more angles of incidence (e.g., an oblique angle of incidence and/or a substantially normal angle of incidence). The optical subsystem may be configured to perform the scanning by scanning the light over the wafer in any suitable manner.

Light scattered from wafer 410 may be collected and detected by multiple channels of the optical subsystem during scanning. For example, light scattered from wafer 410 at angles relatively close to normal may be collected by lens 412. Lens 412 may include a refractive optical element as shown in FIG. 4. In addition, lens 412 may include one or more refractive optical elements and/or one or more reflective optical elements. Light collected by lens 412 may be directed to polarizing component 414, which may include any suitable polarizing component known in the art. In addition, the optical subsystem may include more than one polarizing component (not shown), each of which may be positioned independently in the path of the light collected by the lens. Each of the polarizing components may be configured to alter the polarization of the light collected by the lens in a different manner. The optical subsystem may be configured to move the polarizing components into and out of the path of the light collected by the lens in any suitable manner depending on which polarization setting is selected for detection of the light collected by lens 412 during scanning. The polarization setting used for the detection of the light collected by lens 412 during scanning may include any of the polarization settings described herein (e.g., P, S, and unpolarized (N)).

Light exiting polarizing component 414 is directed to detector 416. Detector 416 may include any suitable detector known in the art such as a charge coupled device (CCD) or another type of imaging detector. Detector 416 is configured to generate output such as an image that is responsive to the scattered light collected by lens 412 and transmitted by polarizing component 414 if positioned in the path of the collected scattered light. Therefore, lens 412, polarizing component 414 if positioned in the path of the light collected by lens 412, and detector 416 form one channel of the optical subsystem. This channel of the optical subsystem may include any other suitable optical components (not shown) known in the art such as a Fourier filtering component.

Light scattered from wafer 410 at different angles may be collected by lens 418. Lens 418 may be configured as described above. Light collected by lens 418 may be directed to polarizing component 420, which may include any suitable polarizing component known in the art. In addition, the optical subsystem may include more than one polarizing component (not shown), each of which may be positioned independently in the path of the light collected by the lens. Each of the polarizing components may be configured to alter the polarization of the light collected by the lens in a different manner. The optical subsystem may be configured to move the polarizing components into and out of the path of the light collected by the lens in any suitable manner depending on which polarization setting is selected for detection of the light collected by lens 418 during scanning. The polarization setting used for detection of the light collected by lens 418 during scanning may include P, S, or N.

Light exiting polarizing component 420 is directed to detector 422, which may be configured as described above. Detector 422 is also configured to generate output such as an image that is responsive to the collected scattered light that passes through polarizing component 420 if positioned in the path of the scattered light. Therefore, lens 418, polarizing component 420 if positioned in the path of the light collected by lens 418, and detector 422 may form another channel of the optical subsystem. This channel may also include any other optical components (not shown) described above. In some embodiments, lens 418 may be configured to collect light scattered from the wafer at polar angles from about 20 degrees to about 70 degrees. In addition, lens 418 may be configured as a reflective optical component (not shown) that is configured to collect light scattered from the wafer at azimuthal angles of about 360 degrees.

The optical subsystem shown in FIG. 4 may also include one or more other channels (not shown). For example, the optical subsystem may include an additional channel, which may include any of the optical components described herein such as a lens, one or more polarizing components, and a detector, configured as a side channel. The lens, the one or more polarizing components, and the detector may be further configured as described herein. In one such example, the side channel may be configured to collect and detect light that is scattered out of the plane of incidence (e.g., the side channel may include a lens, which is centered in a plane that is substantially perpendicular to the plane of incidence, and a detector configured to detect light collected by the lens).

Computer subsystem 404 is configured to acquire the output generated by the optical subsystem. For example, image(s) generated by the detectors during scanning may be provided to computer subsystem 404. In particular, the computer subsystem may be coupled to each of the detectors (e.g., by one or more transmission media shown by the dashed lines in FIG. 4, which may include any suitable transmission media known in the art) such that the computer subsystem may receive the image(s) generated by the detectors. The computer subsystem may be coupled to each of the detectors in any suitable manner.

The computer subsystem is configured for performing the steps of the method described herein. The computer subsystem may also be configured to perform any other step(s) of any method embodiment(s) described herein. The computer subsystem, the optical subsystem, and the system may be further configured as described herein. In addition, although only one computer subsystem is shown in FIG. 4, the system may include more than one computer subsystem, one such as that shown in FIG. 4 that is essentially a part of an overall wafer inspection system and one or more others that may not be part of a wafer inspection system, but may be coupled to a computer subsystem such as that shown in FIG. 4 via one or more transmission media or by a shared storage medium such as a fab database. In this manner, one or more of the steps described herein may be performed by a stand alone computer subsystem that is not actually part of a wafer inspection system.

It is noted that FIG. 4 is provided herein to generally illustrate one configuration of an optical subsystem that may be included in the system embodiments described herein. Obviously, the optical subsystem configuration described herein may be altered to optimize the performance of the optical subsystem as is normally performed when designing a commercial inspection system. In addition, the systems described herein may be implemented using an existing inspection system (e.g., by adding functionality described herein to an existing inspection system) such as the Puma 90xx, 91xx, and 93xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

In additional embodiments, the optical subsystem and/or the computer subsystem(s) described herein may be replaced with one or more virtual inspection systems such as those described in commonly assigned U.S. Pat. No. 8,126,255 issued on Feb. 28, 2012 to Bhaskar et al. and commonly assigned U.S. patent application Ser. No. 14/184,417 filed on Feb. 19, 2014 by Duffy et al., both of which are incorporated by reference as if fully set forth herein. Such methods and systems may be configured to perform any of the step(s) described herein. For example, the output generated by scanning the wafer with the optical mode candidates may be stored in a virtual inspection system, which can then apply different defect detection parameters to the output and perform other steps described herein.

Further modifications and alternative embodiments of various aspects of the invention will be apparent to those skilled in the art in view of this description. For example, methods and systems for setting up wafer inspection recipes are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for setting up a wafer inspection recipe, comprising:

scanning a wafer with a wafer inspection tool and a number of optical mode candidates for the wafer inspection recipe thereby generating output for the wafer for each of the optical mode candidates;

for a first of the optical mode candidates, applying different sets of defect detection parameters to the output generated with the first of the optical mode candidates thereby producing different inspection results for the first of the optical mode candidates, wherein the defect detection parameters are included in defect detection algorithms used with the output generated by scanning the wafer to generate the different inspection results for the wafer, and wherein at least some of the different sets of defect detection parameters are determined based on input from a user;

storing the first of the optical mode candidates with each of the different sets of defect detection parameters as one or more of a number of complete wafer inspection recipe candidates;

repeating the applying and storing steps for at least one other of the optical mode candidates;

comparing the inspection results generated with the complete wafer inspection recipe candidates to each other, wherein no decisions regarding performance of the complete wafer inspection recipe candidates are made until after the comparing step is performed;

determining which of the complete wafer inspection recipe candidates produced the inspection results that are the best based on results of said comparing;

selecting the complete wafer inspection recipe candidate that produced the best inspection results for use as the wafer inspection recipe, wherein the applying, storing, comparing, determining, and selecting steps are performed with one or more computer systems; and comparing the inspection results generated with the complete wafer inspection recipe candidates to requirements for the inspection results received from the user and eliminating any of the complete wafer inspection recipe candidates that did not produce inspection results that meet the requirements from the determining and selecting steps.

2. The method of claim 1, wherein not all of the complete wafer inspection recipe candidates are previously used wafer inspection recipes.

3. The method of claim 1, wherein the optical mode candidates comprise all possible optical modes for use in the wafer inspection recipe.

4. The method of claim 1, wherein at least some of the optical mode candidates are determined based on input from a user.

5. The method of claim 1, further comprising selecting at least some of the optical mode candidates and the different sets of defect detection parameters based on a wafer inspection recipe received as the input from the user.

6. The method of claim 1, further comprising selecting at least some of the optical mode candidates and the different sets of defect detection parameters based on a wafer inspection recipe received as the input from the user with an instruction to generate two or more of the complete wafer inspection recipe candidates that are similar to the wafer inspection recipe received from the user.

7. The method of claim 1, further comprising selecting at least some of the optical mode candidates and the different sets of defect detection parameters based on a wafer inspection recipe received as the input from the user, wherein the wafer inspection recipe received from the user was selected for use as the wafer inspection recipe in a previously performed iteration of the method.

8. The method of claim 1, wherein applying the different sets of defect detection parameters to the output comprises comparing the inspection results produced with a first of the different sets to user-specified targets for the inspection results, altering the first of the different sets based on results of comparing the inspection results produced with the first of the different sets thereby generating a second of the different sets of defect detection parameters, and performing the steps of the applying step with the second of the different sets.

9. The method of claim 1, wherein at least some of the complete wafer inspection recipe candidates are received as the input from the user.

10. The method of claim 1, wherein the selecting step does not comprise selecting optical parameters for use in the wafer inspection recipe followed by selecting defect detection parameters for use in the wafer inspection recipe.

11. The method of claim 1, wherein the method does not comprise selecting optical parameters for use in the wafer inspection recipe followed by selecting defect detection parameters for use in the wafer inspection recipe.

12. The method of claim 1, wherein the method does not comprise eliminating any of the complete wafer inspection recipe candidates prior to comparing the inspection results generated with the complete wafer inspection recipe candidates to each other.

13. The method of claim 1, wherein the inspection results that are compared do not comprise signal-to-noise ratios generated for defects on the wafer by more than one of the complete wafer inspection recipe candidates.

14. The method of claim 1, wherein the inspection results comprise multiple types of information for the wafer generated by each of the complete wafer inspection recipe candidates and for performance of the complete wafer inspection recipe candidates.

15. The method of claim 1, wherein the inspection results comprise information for different types of defects detected on the wafer by each of the complete wafer inspection recipe candidates.

16. A non-transitory computer-readable medium, storing program instructions executable on a computer system for performing a computer-implemented method for setting up a wafer inspection recipe, wherein the computer-implemented method comprises:
scanning a wafer with a wafer inspection tool and a number of optical mode candidates for the wafer inspection recipe thereby generating output for the wafer for each of the optical mode candidates;
for a first of the optical mode candidates, applying different sets of defect detection parameters to the output generated with the first of the optical mode candidates thereby producing different inspection results for the first of the optical mode candidates, wherein the defect detection parameters are included in defect detection algorithms used with the output generated by scanning the wafer to generate the different inspection results for the wafer, and wherein at least some of the different sets of defect detection parameters are determined based on input from a user;
storing the first of the optical mode candidates with each of the different sets of defect detection parameters as one or more of a number of complete wafer inspection recipe candidates;
repeating the applying and storing steps for at least one other of the optical mode candidates;
comparing the inspection results generated with the complete wafer inspection recipe candidates to each other, wherein no decisions regarding performance of the complete wafer inspection recipe candidates are made until after the comparing step is performed;
determining which of the complete wafer inspection recipe candidates produced the inspection results that are the best based on results of said comparing;
selecting the complete wafer inspection recipe candidate that produced the best inspection results for use as the wafer inspection recipe; and
comparing the inspection results generated with the complete wafer inspection recipe candidates to requirements for the inspection results received from the user and eliminating any of the complete wafer inspection recipe candidates that did not produce inspection results that meet the requirements from the determining and selecting steps.

17. A system configured to set up a wafer inspection recipe, comprising:
an optical subsystem configured to scan a wafer with a number of optical mode candidates for the wafer inspection recipe thereby generating output for the wafer for each of the optical mode candidates; and
one or more computer subsystems configured for:
for a first of the optical mode candidates, applying different sets of defect detection parameters to the output generated with the first of the optical mode candidates thereby producing different inspection results for the first of the optical mode candidates, wherein the defect detection parameters are included in defect detection algorithms used with the output generated by scanning the wafer to generate the different inspection results for the wafer, and wherein at least some of the different sets of defect detection parameters are determined based on input from a user;
storing the first of the optical mode candidates with each of the different sets of defect detection parameters as one or more of a number of complete wafer inspection recipe candidates;
repeating the applying and storing steps for at least one other of the optical mode candidates;
comparing the inspection results generated with the complete wafer inspection recipe candidates to each other, wherein no decisions regarding performance of the complete wafer inspection recipe candidates are made until after the comparing step is performed;
determining which of the complete wafer inspection recipe candidates produced the inspection results that are the best based on results of said comparing;
selecting the complete wafer inspection recipe candidate that produced the best inspection results for use as the wafer inspection recipe; and
comparing the inspection results generated with the complete wafer inspection recipe candidates to requirements for the inspection results received from the user and eliminating any of the complete wafer inspection recipe candidates that did not produce inspection results that meet the requirements from the determining and selecting steps.

18. The system of claim 17, wherein not all of the complete wafer inspection recipe candidates are previously used wafer inspection recipes.

19. The system of claim 17, wherein the optical mode candidates comprise all possible optical modes for use in the wafer inspection recipe.

20. The system of claim 17, wherein at least some of the optical mode candidates are determined based on input from a user.

21. The system of claim 17, wherein the one or more computer subsystems are further configured for selecting at least some of the optical mode candidates and the different sets of defect detection parameters based on a wafer inspection recipe received as the input from the user.

22. The system of claim 17, wherein the one or more computer subsystems are further configured for selecting at least some of the optical mode candidates and the different sets of defect detection parameters based on a wafer inspection recipe received as the input from the user with an instruction to generate two or more of the complete wafer inspection recipe candidates that are similar to the wafer inspection recipe received from the user.

23. The system of claim 17, wherein the one or more computer subsystems are further configured for selecting at least some of the optical mode candidates and the different sets of defect detection parameters based on a wafer inspection recipe received as the input from the user, and wherein the wafer inspection recipe received from the user was selected for use as the wafer inspection recipe in a previously performed iteration of the method.

24. The system of claim 17, wherein applying the different sets of defect detection parameters to the output comprises comparing the inspection results produced with a first of the different sets to user-specified targets for the inspection results, altering the first of the different sets based on results of comparing the inspection results produced with the first of the different sets thereby generating a second of the different sets of defect detection parameters, and performing the steps of the applying step with the second of the different sets.

25. The system of claim 17, wherein at least some of the complete wafer inspection recipe candidates are received as the input from the user.

26. The system of claim 17, wherein the selecting step does not comprise selecting optical parameters for use in the wafer inspection recipe followed by selecting defect detection parameters for use in the wafer inspection recipe.

27. The system of claim 17, wherein the one or more computer subsystems are not configured for selecting optical parameters for use in the wafer inspection recipe followed by selecting defect detection parameters for use in the wafer inspection recipe.

28. The system of claim 17, wherein the one or more computer subsystems are not configured for eliminating any of the complete wafer inspection recipe candidates prior to comparing the inspection results generated with the complete wafer inspection recipe candidates to each other.

29. The system of claim 17, wherein the inspection results that are compared do not comprise signal-to-noise ratios generated for defects on the wafer by more than one of the complete wafer inspection recipe candidates.

30. The system of claim 17, wherein the inspection results comprise multiple types of information for the wafer generated by each of the complete wafer inspection recipe candidates and for performance of the complete wafer inspection recipe candidates.

31. The system of claim 17, wherein the inspection results comprise information for different types of defects detected on the wafer by each of the complete wafer inspection recipe candidates.

\* \* \* \* \*